United States Patent
Uchimura

(10) Patent No.: US 10,583,434 B2
(45) Date of Patent: Mar. 10, 2020

(54) FUNCTIONAL MATERIAL, METHOD FOR PRODUCING FUNCTIONAL MATERIAL, AND FUNCTIONAL LIQUID

(71) Applicant: NATIONAL UNIVERSITY CORPORATION EHIME UNIVERSITY, Matsuyama-shi, Ehime (JP)

(72) Inventor: Hiromi Uchimura, Shikokuchuo (JP)

(73) Assignee: NATIONAL UNIVERSITY CORPORATION EHIME UNIVERSITY, Matsuyama-shi, Ehime (JP)

(*) Notice: Subject to any disclaimer, the term of this patent is extended or adjusted under 35 U.S.C. 154(b) by 519 days.

(21) Appl. No.: 15/300,557

(22) PCT Filed: Mar. 31, 2015

(86) PCT No.: PCT/JP2015/060241
§ 371 (c)(1),
(2) Date: Sep. 29, 2016

(87) PCT Pub. No.: WO2015/152287
PCT Pub. Date: Oct. 8, 2015

(65) Prior Publication Data
US 2017/0113220 A1    Apr. 27, 2017

(30) Foreign Application Priority Data
Mar. 31, 2014    (JP) .................... 2014-071205

(51) Int. Cl.
*B01L 3/00*    (2006.01)
*B81B 7/00*    (2006.01)
(Continued)

(52) U.S. Cl.
CPC ....... *B01L 3/502707* (2013.01); *B01L 3/5023* (2013.01); *B81B 7/00* (2013.01);
(Continued)

(58) Field of Classification Search
CPC ............ B01L 3/502707; B01L 3/5023; B01L 2300/161; B01L 2200/12;
(Continued)

(56) References Cited

U.S. PATENT DOCUMENTS

2006/0159916 A1*    7/2006    Dubrow ............. B01J 20/28007
428/357
2007/0274862 A1    11/2007    Harttig
2010/0233033 A1*    9/2010    Horiuchi ........... B01L 3/502707
422/401

FOREIGN PATENT DOCUMENTS

JP    2008-523356 A    7/2008
JP    2012-159440 A    8/2012
(Continued)

OTHER PUBLICATIONS

International Search Report of PCT/JP2015/060241.

*Primary Examiner* — Samuel P Siefke
(74) *Attorney, Agent, or Firm* — Muncy, Geissler, Olds & Lowe, P.C.

(57) ABSTRACT

Disclosed herein is a functional material having the function of detecting a predetermined substance or the like present in a sample with high accuracy even when the amount of the sample is small, and a method for producing the functional material. The functional material includes a channel part 10 that allows a liquid to pass therethrough, and the channel part 10 is made of a water-permeable material 11 containing a water-impermeable material 12. The water-impermeable material 12 is placed between pieces of the water-permeable material 11, and therefore voids 10h can be formed between the water-impermeable material 12 and the water-permeable (Continued)

material 11. That is, a network of the voids 10*h* can be formed in the channel part 10. A liquid sample supplied to the channel part 10 is allowed to move while being allowed to penetrate into the voids 10*h*. In addition, components other than a desired component can be separated and removed from a mixture present in the liquid sample while the liquid sample is allowed to move. Therefore, a water-absorbing function and a filtering function can be imparted to the channel part 10.

13 Claims, 12 Drawing Sheets

(51) Int. Cl.
*G01N 35/10* (2006.01)
*G01N 35/00* (2006.01)

(52) U.S. Cl.
CPC ... *B01L 2200/12* (2013.01); *B01L 2300/0816* (2013.01); *B01L 2300/0887* (2013.01); *B01L 2300/161* (2013.01); *B01L 2400/0406* (2013.01); *G01N 2035/00237* (2013.01); *G01N 2035/1034* (2013.01)

(58) Field of Classification Search
CPC ..... B01L 2400/0406; B01L 2300/0887; B01L 2300/0816; B81B 7/00; G01N 2035/1034; G01N 2035/00237
See application file for complete search history.

(56) References Cited

FOREIGN PATENT DOCUMENTS

| | | |
|---|---|---|
| JP | 2012-230125 A | 11/2012 |
| WO | 2008/001737 A1 | 1/2008 |

\* cited by examiner

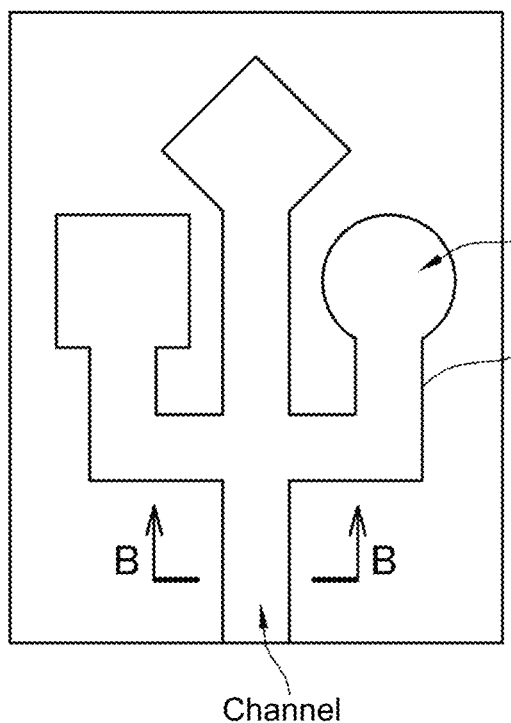
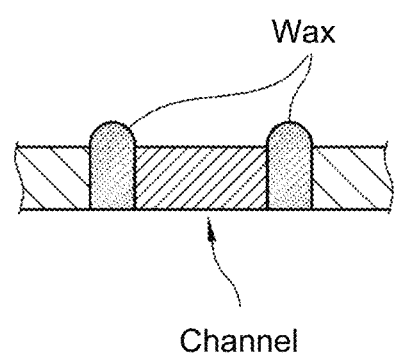
Fig. 6(A)
Fig. 6(B)
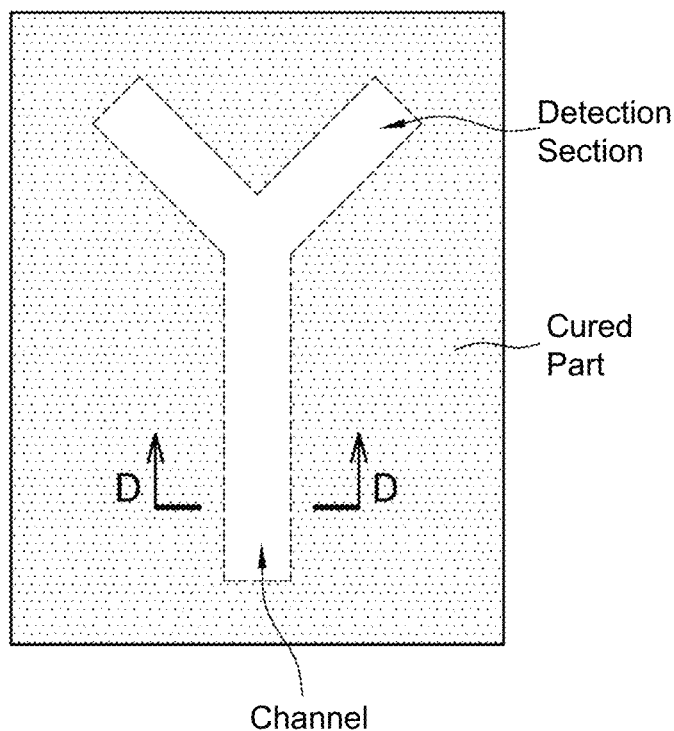
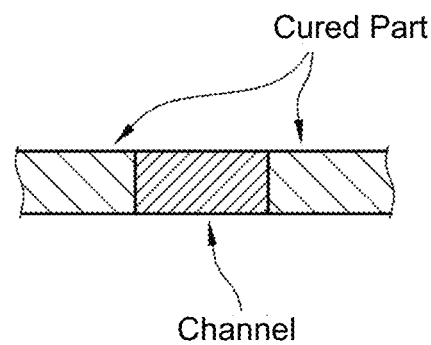
Fig. 6(C)
Fig. 6(D)

1 cm.

Just Before Start

Dropping

After 1 Second From Dropping

After 5 Seconds From Dropping

After 30 Seconds From Dropping

After 60 Seconds From Dropping

After 90 Seconds From Dropping

After 120 Seconds From Dropping

FUNCTIONAL MATERIAL, METHOD FOR PRODUCING FUNCTIONAL MATERIAL, AND FUNCTIONAL LIQUID

TECHNICAL FIELD

The present invention relates to a functional material, a method for producing a functional material, and a functional liquid. More specifically, the present invention relates to a functional material to be widely used for analysis in medical, biochemical, pharmaceutical, chemical, and environmental fields, a method for producing a functional material, and a functional liquid.

BACKGROUND ART

In recent years, it has become possible to diagnose many diseases from body fluid such as blood or urine. However, there is a limit on the amount of body fluid that can be used for diagnosis (hereinafter, referred to as a sample). Therefore, it has become important to develop a device that makes it possible to obtain as much information as possible (e.g., the degree of progression of disease or the early detection of disease) from a small amount of sample.

A device has been proposed which uses a micro-fluid chip including a resin substrate and two or more microchannels formed on the resin substrate. At the tip end of each of the microchannels provided on the substrate of the device, a detection section is provided which includes an antibody or the like that reacts with an antigen that causes each disease. Therefore, the use of such a device makes it possible to diagnose two or more diseases by a single analysis. However, such a device requires a driving means such as a pump to send a sample into the channels, which causes a problem that the device requires a certain amount of sample and increases in size.

In recent years, a micro-fluid chip that requires no pump has been proposed. A typical example of such a micro-fluid chip is a paper-made micro-fluid chip whose microchannels are made of paper. Such a paper-made micro-fluid chip is based on a technique using the water absorbability of paper, that is, capillarity. More specifically, when a liquid sample is supplied to the base ends of the channels of the paper-made micro-fluid chip, the sample automatically moves from the base ends of the channels to detection sections provided at the tip ends of the channels. Therefore, two or more diseases can be diagnosed by a single analysis without using a pump for sending a sample. In addition, there is an advantage that disease diagnosis can be performed only by the paper-made micro-fluid chip.

As a method for forming such paper-made microchannels as described above, a method using wax printing or a method using photolithography has been proposed.

In the case of wax printing, a sheet of paper is impregnated with a hydrophobic wax along the side edges of channels on the sheet of paper. As a result, as shown in FIG. 6(A) and FIG. 6(B), paper-made microchannels are formed by forming channel walls made of the hydrophobic wax.

In the case of photolithography, paper is immersed in a photoresist (photosensitive resin), and is then masked so that a desired channel pattern can be formed, and is then exposed to UV or the like. Then, the unexposed photoresist is removed. As a result, as shown in FIG. 6(C) and FIG. 6(D), paper-made microchannels are formed by forming channel walls made of the cured resin (cured part).

However, in the case of such paper-made microchannels formed by the above method, a sample containing a plurality of components moves through all the channels. Therefore, there is a possibility that the accuracy of measurement of a desired component at each of the detection sections is reduced due to the influence of components other than the desired component contained in the sample.

Meanwhile, a micro-fluid chip has been proposed which has three-dimensional channels formed by photolithography (e.g., Patent Document 1).

As shown in FIG. 7 (A) and FIG. 7 (B), the three-dimensional micro-fluid chip described in Patent Document 1 has a multi-layer structure in which slips of paper processed by photolithography are coupled together as top, middle, and bottom layers. The slip of paper as a middle layer is formed to have holes through which the front and back surfaces thereof communicate with each other so that only a predetermined channel in the upper layer and a predetermined channel in the bottom layer are connected together through the holes. Further, Patent Document 1 describes that a filter is provided in the holes formed in the middle layer.

Therefore, as shown in FIG. 7(C), when two samples are supplied to their respective channels, which three-dimensionally intersect with each other, of the three-dimensional micro-fluid chip described in Patent Document 1, both the samples are allowed to move from the sample supply sections to the tip ends of the channels without being mixed together. Therefore, the use of the three-dimensional micro-fluid chip described in Patent Document 1 makes it possible to analyze more samples and improve the accuracy of a test due to a filtering function as compared to a case where two-dimensional channels are formed in a chip of the same size.

PRIOR ART DOCUMENTS

Patent Document

Patent Document 1: JP-A-2012-230125

SUMMARY OF THE INVENTION

Problems to be Solved by the Invention

As shown in FIG. 7, the three-dimensional micro-fluid chip described in Patent Document 1 is required to be formed so that the channels three-dimensionally intersect with each other to prevent mixing of samples. Therefore, the distance between the sample supply section to the detection section of each of the channels is much longer than that of such a paper-made two-dimensional microchannel as described above. Therefore, when the amount of a sample is small, there is a possibility that the movement of the sample is interrupted on the way in one of the channels so that a sufficient amount of the sample does not reach the detection section. In this case, there is a risk that a diagnostic error is caused due to a reduction in the accuracy of a disease diagnostic test at the detection section.

In view of the above circumstances, it is an object of the present invention to provide a functional material that has the function of detecting a predetermined substance present in a sample with high accuracy even when the amount of the sample is small, a method for producing a functional material, and a functional liquid.

Means for Solving the Problem

A first invention is a functional material comprising: a base material; and a channel part that is provided on a surface of the base material and that allows a liquid to pass therethrough, wherein the base material has a water-impermeable surface, and the channel part is made of a water-permeable material containing a water-impermeable material.

A second invention is the functional material according to the first invention, comprising a channel part that allows a liquid to pass therethrough, wherein the channel part is made of a water-permeable material containing a water-impermeable material.

A third invention is the functional material according to the second invention, comprising a base material, wherein the channel part is formed on a surface of the base material.

A fourth invention is the functional material according to the second invention, wherein the water-permeable material comprises fibers.

A fifth invention is a functional material comprising: a base material; and a channel part that is provided on a surface of the base material and that allows a liquid to pass therethrough, wherein the base material has a water-impermeable surface, and the channel part comprises nano-fiber layers comprising nano-fibers and a water-impermeable material trapped between the nano-fiber layers.

A sixth invention is the functional material according to the second invention, wherein the water-impermeable material is a fibrous material and comprises materials different in fiber diameter and/or fiber length.

A seventh invention is the functional material according to the second invention, comprising a base material having a surface on which the channel part is formed, wherein the water-permeable material has a hydrophilic functional group, and the base material has a mounting surface on which the channel part is provided, the mounting surface being covered with a water-impermeable film having hydrophilic functional groups.

An eighth invention is a method for producing a functional material, comprising forming, on a mounting surface of a base material, a channel part that allows a liquid to pass therethrough, wherein the channel part is formed by applying a mixed fluid containing a water-impermeable material, a water-permeable material, and a liquid that disperses both of them.

A ninth invention is a method for producing a functional material comprising forming, on a mounting surface of a base material, a channel part that allows a liquid to pass therethrough, wherein the channel part is formed by applying a mixed fluid containing a water-impermeable material, nano-fibers, and a liquid that disperses both of them.

A tenth invention is the method for producing a functional material according to the eighth invention, wherein the channel part is formed by applying the mixed fluid onto the mounting surface of the base material with use of a screen printing technique.

An eleventh invention is the method for producing a functional material according to the eighth invention, wherein the channel part is formed by spraying the mixed fluid onto the mounting surface of the base material.

A twelfth invention is the method for producing a functional material according to the eighth invention, wherein the channel part is formed using the mixed fluid as a raw material on the mounting surface of the base material with use of an intaglio printing technique.

A thirteenth invention is the method for producing a functional material according to the eighth invention, wherein the channel part is formed using the mixed fluid as a raw material on the mounting surface of the base material with use of a flexographic printing technique.

A fourteenth invention is a functional liquid for use in printing, which is obtained by dispersing a water-permeable material and a water-impermeable material in a liquid.

A fifteenth invention is the functional liquid according to the fourteenth invention, wherein the water-permeable material comprises fibers.

A sixteenth invention is a functional material according to the second invention, wherein the channel part comprises a plurality of pieces of a water-permeable material that comprises fibers and that allows the liquid to pass through its inside by capillarity, a plurality of pieces of a water-impermeable material placed between the pieces of the water-permeable material, and voids that are provided between the pieces of the water-permeable material and that allow the liquid to pass through them by capillarity.

A seventeenth invention is a functional liquid for use in printing according to the fourteenth invention, which is obtained by dispersing nano-fibers and a water-impermeable material in a liquid.

Effect of the Invention

According to the first invention, the water-impermeable material is placed between pieces of the water-permeable material, which makes it possible to form voids between the water-impermeable material and the water-permeable material. That is, a network of voids can be formed in the channel part. Therefore, a liquid sample supplied to the channel part is allowed to move while penetrating into the voids. In addition, components other than a desired component (undesired components) can be separated and removed from a mixture present in the liquid sample while the liquid sample is allowed to move. That is, a water-absorbing function and a filtering function can be imparted to the channel part.

According to the third invention, the channel part is formed on the surface of the base material, which makes it possible to improve handleability. In addition, formation of the channel part on the surface of the base material makes it possible to improve the degree of freedom of the shape of the channel part.

According to the fourth invention, the water-permeable material includes fibers, which makes it possible to move a liquid sample, which has penetrated between the fibers, by capillarity. This makes it possible to improve the water-absorbing function of the channel part. Further, since the liquid sample moves within the channel part by capillarity, a direction in which the channel part is placed is not limited to a horizontal direction. This makes it possible to increase the degree of freedom of a method in which the channel part is placed after the liquid sample is supplied.

According to the fifth invention, the water-impermeable material is trapped between the nano-fiber layers in the channel part, which makes it possible to form minute voids between the nano-fiber layers. Therefore, a liquid sample supplied to the channel part is allowed to move within the channel part by capillarity while penetrating into the voids. That is, a water-absorbing function can be imparted to the channel part. In addition, the liquid sample is allowed to flow through the voids formed between the nano-fiber layers while penetrating into the voids, and therefore components other than a desired component (undesired components) can be separated and removed from a mixture present in the liquid sample. That is, a filtering function can be imparted to the channel part. Further, the surface of the channel part can be covered with a film having the nano-fiber layers, which makes it possible to prevent the liquid sample from leaking from the inside to the outside of the channel part.

According to the sixth invention, the penetration rate of a liquid sample supplied to the channel part can be adjusted, and therefore the channel part can be formed depending on, for example, the properties of the liquid sample or a desired component present in the liquid sample.

According to the seventh invention, the materials each having a hydrophilic functional group can be brought into contact with each other in a state where the channel part is provided on the mounting surface of the base material. Both of them can be coupled together by hydrogen bonding by bringing them into contact with each other. Therefore, the channel part and the base material can reliably be coupled together simply by providing the channel part on the mounting surface of the base material by application or the like. Further, the channel part can be tightly coupled to the base material, which eliminates the need for an adhesive or the like for coupling them together. This makes it possible to prevent contamination of the channel part caused by an adhesive or the like, thereby improving the accuracy of analysis of a desired component present in a liquid sample.

According to the eighth and thirteenth inventions, a channel part can be formed using a mixed fluid that is in a predetermined state, which makes it possible to improve the degree of freedom in forming a channel part. This makes it possible to simply form a large number of channel parts having a desired pattern.

According to the fourteenth invention, the water-permeable material and the water-impermeable material are dispersed in the liquid. Therefore, a channel including the water-permeable material and the water-impermeable material can be formed on an object by printing the liquid on the object. Further, printing makes it possible to freely form a channel on an object.

According to the fifteenth invention, the water-permeable material contained in the liquid includes fibers, which makes it possible to form, between the fibers, voids into which a liquid sample is allowed to penetrate by capillarity. This makes it possible to form a channel part having a high water-absorbing function.

According to the sixteenth invention, the water-permeable material comprises fibers so that minute gaps are formed in the water-permeable material, which allows a liquid to pass through the inside of the water-permeable material by capillarity. Further, the water-impermeable material is placed between the fibers, which makes it possible to form a network of voids, through which a liquid can pass by capillarity, also between the water-impermeable material and the fibers, that is, in the channel part. Therefore, a liquid sample supplied to the channel part is allowed to move along the fibers of the water-permeable material while penetrating into the gaps in the water-permeable material and the voids. That is, the liquid sample that has penetrated between the fibers and the liquid sample that has entered the voids are allowed to move by capillarity, which makes it possible to improve the water-absorbing function of the channel part. In other words, the channel part can have a water-absorbing function that cannot be obtained simply by having the network of voids. Further, components other than a desired component (undesired components) can be separated and removed from a mixture present in the liquid sample while the liquid sample moves through the gaps and the voids. That is, the channel part can have both a water-absorbing function and a filtering function. Further, the liquid sample moves within the channel part by capillarity, and therefore a direction in which the channel part is placed is not limited to a horizontal direction. This makes it possible to increase the degree of freedom of a method in which the channel part is placed after the liquid sample is supplied. Further, the size of the voids or a void ratio can be controlled by adjusting the mixing ratio between the water-permeable material and the water-impermeable material, which makes it possible to control the water absorbability of the channel part.

According to the seventeenth invention, the water-permeable material comprising nano-fibers and the water-impermeable material are dispersed in the liquid, which makes it possible to form a channel comprising the fibers and the water-impermeable material on an object by printing the liquid on the object. This makes it possible to form, between the fibers, voids into which a liquid sample is allowed to penetrate by capillarity. This makes it possible to form a channel part having a high water-absorbing function. In addition, printing makes it possible to freely form a channel on an object.

BRIEF DESCRIPTION OF THE DRAWINGS

FIG. 2 shows a schematic sectional view of a channel part 10 of the functional material 1 according to the embodiment of the present invention and illustrations showing a situation in which a liquid sample is supplied to the channel part 10, wherein

FIG. 4 shows schematic sectional views of the channel part 10 of the functional material 1 according to the embodiment of the present invention and illustrations showing a situation in which a liquid sample is supplied to the channel part 10, wherein

FIG. 6(A) is a schematic view illustrating a conventional technique using wax printing, and FIG. 6(B) is a schematic view illustrating a conventional technique using photolithography.

MODE FOR CARRYING OUT THE INVENTION

Figure 1A:
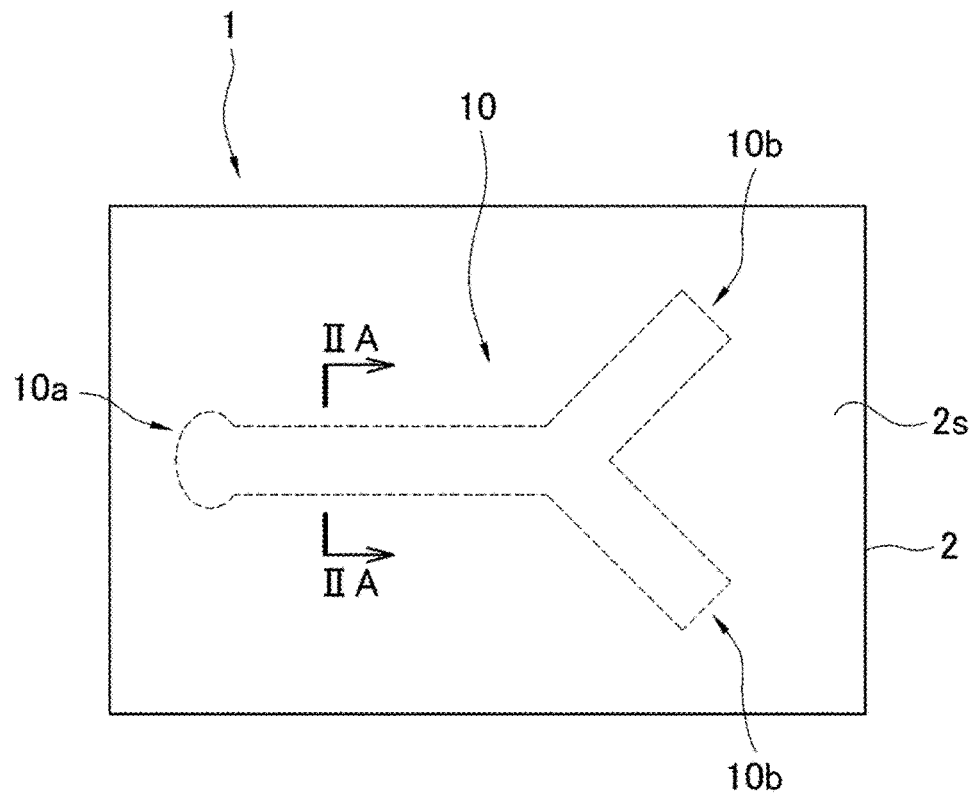
FIG. 1(A) is a schematic plan view illustrating a functional material 1 according to an embodiment of the present invention.

Hereinbelow, an embodiment of the present invention will be described based on the drawings.

A functional material according to the present invention is intended to be used for sample analysis in medical, biochemical, pharmaceutical, chemical, and environmental fields, and has a structure capable of easily separating a desired component present in a sample from components other than the desired component.

More specifically, a channel part constituting the functional material according to the present invention has a structure that has a water-absorbing function and a filtering function and that is capable of reducing the amount of a sample used.

A difference between a conventional technique and the present invention will briefly be described.

First, in the case of a conventional technique (e.g., a micro-fluid chip), a water-permeable region and a water-impermeable region are provided in a sheet of paper to form a channel through which a liquid is allowed to move to a desired position (e.g., a position where a reagent is placed). That is, the conventional technique is based on the idea that a region (channel) through which a liquid passes (penetrates) is formed by providing, in a sheet of paper itself, a portion through which a liquid passes and a portion (wall) through which a liquid does not pass. Therefore, in the conventional technique, part of a base material functions as a channel.

On the other hand, in the case of the functional material according to the present invention, a channel is formed on the surface of a base material such as a sheet by printing a liquid containing fibers (in other words, a fiber-containing ink) on the surface of the base material. That is, the functional material according to the present invention is not based on a technique in which a channel is formed by altering a base material but based on a technique in which a channel including fibers contained in a fiber-containing ink is formed by forming a pattern using the fiber-containing ink on the surface of a base material. Therefore, the functional material according to the present invention has a raised channel on a base material.

That is, the present invention is completely different from the conventional technique in a method for forming a channel (technical idea).

In the case of the functional material according to the present invention, a channel is formed by printing a fiber-containing ink, and therefore there are the following merits.

In the case of the conventional technique, wax printing or photolithography is used to form a channel, but such a method requires a complicated process.

On the other hand, in the case of the functional material according to the present invention, a channel can easily be formed simply by printing a fiber-containing ink on a base material.

Further, in the case of the conventional technique, a water-impermeable portion is formed in paper, but a water-permeable portion still has the properties of the original paper. Therefore, when a test tool based on the conventional technique is used, foreign substances other than a desired component contained in a liquid sample are also supplied, which reduces detection accuracy.

On the other hand, in the case of the functional material according to the present invention, the fiber-containing ink may contain a material other than fibers, which makes it possible to add a function other than the penetration of a liquid to the channel. More specifically, a filtering effect can be imparted to the channel by mixing water-impermeable fibers. Therefore, when the functional material according to the present invention is used as a test tool, a liquid sample from which foreign substances have been removed can reach the tip end of the channel part, which is advantageous in that a desired component present in the liquid sample can be detected with high accuracy.

Further, the amount of voids in the channel can be controlled by mixing, in a predetermined ratio, fibers having a large fiber diameter and fibers having a small fiber diameter or fibers having a large fiber length or fibers having a small fiber length as water-impermeable fibers contained in the fiber-containing ink. This makes it possible to control the penetration rate of a liquid supplied to the channel of the functional material according to the present invention.

As described above, the functional material according to the present invention is completely different from the conventional technique in a method for forming a channel (technical idea), and has a superior effect to the conventional technique due to a difference in the structure of a channel formed based on such a difference in idea.

It is to be noted that when the functional material according to the present invention is used for analysis, components present in a liquid sample to be supplied to the channel part of the functional material are not particularly limited as long as the liquid sample is a sample in a solution state or a sample dissolved in a liquid (hereinafter, simply referred to as a liquid sample). Examples of such a liquid sample include blood, environmental water such as river water, and industrial liquid waste discharged from factories.

Further, the functional material according to the present invention is not limited to one including a channel part that allows a liquid to pass therethrough and a base material for holding the channel part, and may be one including only a channel part. For example, as will be described later, after forming a channel part of the functional material according to the present invention, only the channel part may directly be used.

The functional material according to the present invention can basically be produced by a simple process of just applying a dispersion liquid, which makes it possible to improve productivity and economic efficiency. Further, such a simple production process is advantageous also in that the convenience of quality evaluation can be improved.

Hereinbelow, the functional material according to the present invention will be described with reference to its typical example including a channel part that allows a liquid to pass therethrough and a base material for holding the channel part.

Figure 1B:
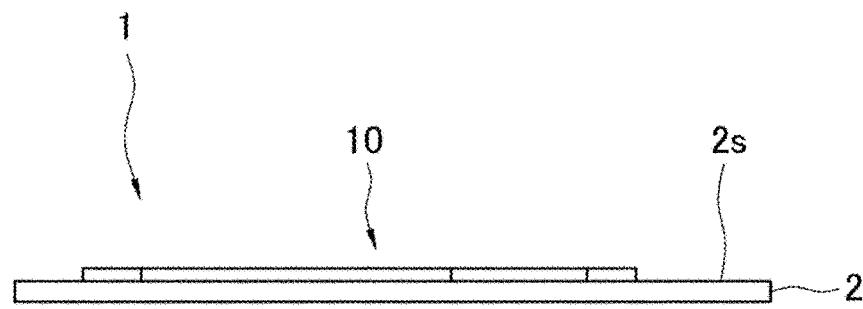
FIG. 1(B) is a schematic side view of the functional material 1 shown in FIG. 1(A).

As shown in FIG. 1, a functional material 1 according to an embodiment of the present invention (hereinafter, simply referred to as a functional material 1) includes a channel part 10 that allows a liquid to pass therethrough and a base material 2 that holds the channel part 10.

(Description of Base Material 2)

The shape and size of the base material 2 are not particularly limited as long as the base material 2 is formed to have a surface 2s on which the channel part 10 can be provided and by which the channel part 10 can be held.

For example, as shown in FIG. 1, the channel part 10 having a substantially Y shape in plan view is provided on the surface 2s of the base material 2 having a rectangular shape in plan view so as to be parallel to the longitudinal direction of the base material 2. At this time, the channel part 10 is provided so as to be located inside the edge of the base material 2. By providing the channel part 10 on the surface 2s of the base material 2 in such a state as described above, the channel part 10 is held by the base material 2. Therefore, the functional material 1 can be transferred to a desired place without contact with the channel part 10 by carrying the functional material 1 while grasping a portion of the base material 2 where the channel part 10 is not provided. This makes it possible to prevent the contamination of the channel part 10 of the functional material 1, which is preferred from an analytical viewpoint.

Further, since the channel part 10 is transferred without directly grasping the channel part 10, there is no risk of breakage or functional decline of the channel part 10, which makes it possible to improve the handleability of the functional material 1. In addition, since the channel part 10 is provided on the surface 2s of the base material 2, as will be described later, it is possible to increase the degree of freedom in forming the channel part 10.

It is to be noted that the above example has been described with reference to a case where the base material 2 of the functional material 1 is formed to have a larger size than the channel part 10, but the size of the base material 2 is not limited thereto. The base material 2 may be formed to have substantially the same size as the channel part 10. More specifically, the base material 2 may be formed so that edges 10e of the base end and the tip ends of the channel part 10 are substantially flush with the edge of the base material 2 (see FIG. 5) or are located slightly outside the edge of the base material 2. The details will be described later.

It is to be noted that the material of the base material 2 of the functional material 1 is not particularly limited as long as the channel part 10 can be provided on the surface of the material. Examples of such a material include paper such as Japanese paper, packing paper, paper board, corrugated cardboard base paper, and laminated paper, polyethylene films, and plate-like members made of metal. Particularly, in a case where the base material 2 is made of a hydrophilic material (including a case where a water-impermeable material is contained), as will be described later, the base material 2 and the channel part 10 are coupled together by hydrogen bonding when the channel part 10 has a water-permeable material. That is, in a case where the base material 2 has a hydrophilic functional group, the functional material 1 in which the channel part 10 is provided on the base material 2 can be formed without using an adhesive or the like.

However, in a case where a paper material is used as the material of the base material 2, there is a possibility that a liquid sample supplied to the channel part 10 of the functional material 1 penetrates from the inside of the channel part 10 to the inside of the base material 2 through the contact surface between the channel part 10 and the base material 2. Therefore, in a case where a liquid-permeable material is used, the base material 2 is preferably formed so that the surface 2s has water resistance.

The base material 2 whose surface 2s has water resistance can be formed by, for example, forming a water resistant layer having water resistance as a layer having the surface 2s. The material of this water resistant layer is not particularly limited as long as a liquid such as water does not penetrate to the inside of the base material 2. Examples of such a water resistant layer include an assembly of tangled nano-fibers nf made of cellulose (hereinafter, simply referred to as cellulose nano-fibers nf) (hereinafter, referred to as a cellulose nano-fiber layer) and a film layer formed from a synthetic resin film. Particularly, a cellulose nano-fiber layer is preferably formed as a surface layer of the base material 2 because, as will be described later, the surface 2s of the base material 2 and the channel part 10 can be tightly coupled together.

It is to be noted that when the base material 2 is formed to have a substantially flat surface, the channel part 10 that will be described later can have a uniform thickness, and therefore as will be described later, a liquid sample supplied to the channel part 10 is allowed to substantially uniformly move within the channel part 10.

The surface 2s of the base material 2 in this description corresponds to a mounting surface of a base material in claims.

(Description of Channel Part 10)

As shown in FIG. 2, the channel part 10 includes a water-permeable material 11 and a water-impermeable material 12.

It is to be noted that the shape and size of the channel part 10 are not particularly limited. The channel part 10 may have a substantially I shape in plan view, a substantially Y shape in plan view (see FIG. 1), a fan-like pattern, a radial pattern, or the like.

For example, as shown in FIG. 1, when formed to have a substantially Y shape in plan view, the channel part 10 can have a channel thickness of about 0.02 to 5 mm and a channel width of about 0.5 to 50 mm.

Further, the channel part 10 is preferably formed so that a base end 10a of the channel part 10 can temporarily hold a liquid sample supplied to the channel part 10 of the functional material 1.

For example, as shown in FIG. 1, the base end 10a of the channel part 10 is formed to have a substantially circular shape whose diameter is slightly larger than the channel width. When a liquid sample is supplied to the base end 10a having such a shape, the supplied liquid sample is temporarily held in the base end 10a of the channel part 10, and is then allowed to substantially uniformly move within the channel part 10 toward tip ends 10b of the channel part 10.

It is to be noted that, as shown in FIG. 1, a detection material that reacts with a desired component contained in a liquid sample may be supported by each of the tip ends 10b of the channel part 10. In this case, as will be described later, when a liquid sample is supplied to the channel part 10 of the functional material 1 so as to move within the channel part 10 from the base end 10a to the tip ends 10b, it is possible to easily determine whether or not a desired component is present in the liquid sample. This detection material can appropriately be selected from various reaction reagents for antigen-antibody reaction or fluorescence reaction depending on a desired component contained in the liquid sample.

(Water-Permeable Material 11)

The water-permeable material 11 is not particularly limited as long as the water-permeable material 11 has the property of allowing a liquid such as water to penetrate to its inside or the property of allowing a liquid such as water to flow along its surface.

Figure 2A:
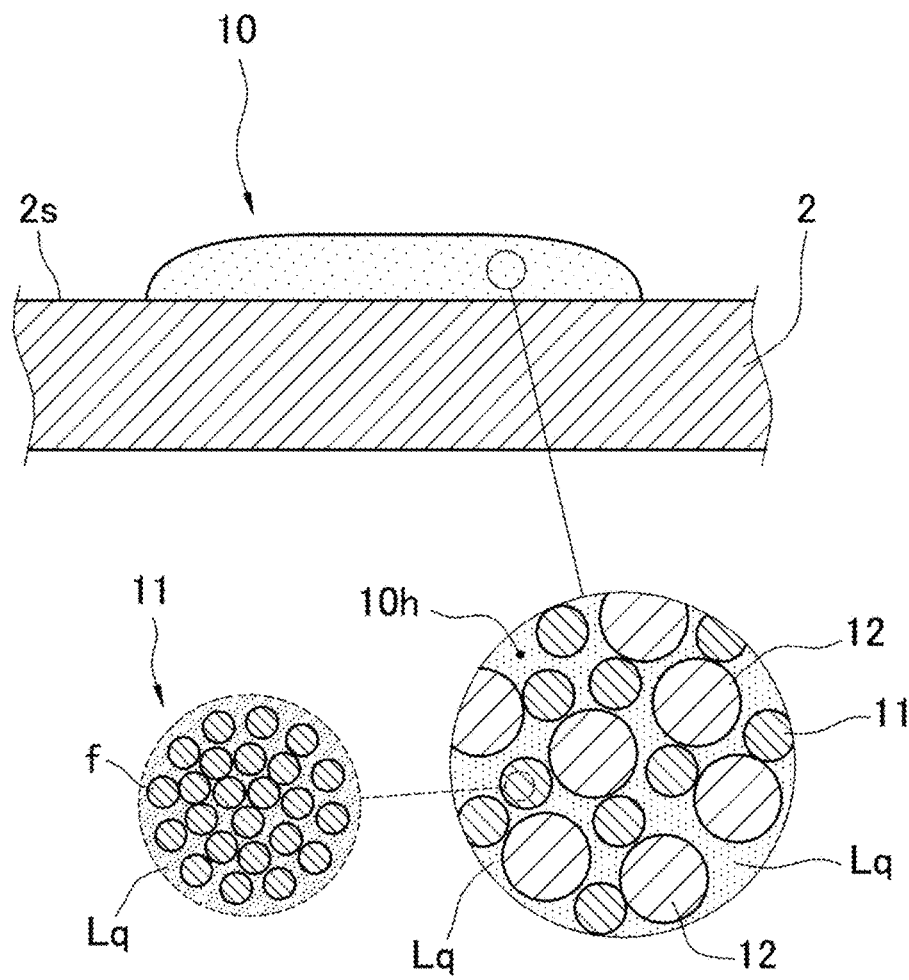
FIG. 2(A) shows a schematic sectional view taken along a line IIA-IIA in FIG. 1(A), an enlarged sectional view of a major part of the channel part 10, and an enlarged view of a major part of a water-permeable material 11.

For example, as shown in the enlarged view of the water-permeable material 11 in FIG. 2(A), the water-permeable material 11 may be a fiber assembly in which a plurality of fine fibers f are bundled together. The fiber diameter or fiber length of each of the fibers f constituting the fiber assembly is not particularly limited, but for example, fibers having a fiber diameter of about 1 to 50 μm and a fiber length of about 0.1 to 10 mm may be used.

Further, the material of the fibers f constituting the water-permeable material 11 is not particularly limited, and examples of the material that can be used include fibers made of a natural material such as cotton or linen (natural fibers) and fibers made of a synthetic resin such as rayon mainly made of cellulose or polyvinyl alcohol (PVA) (chemical fibers). A mixture obtained by appropriately mixing both of them may, of course, be used.

(Water-Impermeable Material 12)

The water-impermeable material 12 is made of a material that does not allow a liquid such as water to penetrate to its inside. The size and shape of the water-impermeable material 12 are not particularly limited as long as the water-impermeable material 12 can be provided to be located between pieces of the above-described water-permeable material 11. Examples of the water-impermeable material 12 that can be used include materials having various shapes such as a block, a sphere, and a fiber.

Further, the material of the water-impermeable material 12 is not particularly limited as long as the material poorly reacts with components contained in a liquid sample supplied to the channel part 10 of the functional material 1 according to the present invention. Examples of the material include synthetic resins such as polyethylene terephthalate (PET), polyethylene (PE), and polypropylene (PP), calcium carbonate, and silicon dioxide, but the material is preferably one that poorly reacts with components present in a liquid sample.

For example, when an animal body fluid such as blood is used as a liquid sample, the water-impermeable material 12 is preferably made of PET that is less reactive with such a liquid.

When PET is used as a raw material of the water-impermeable material 12, there is an advantage that the water-impermeable material 12 can uniformly be formed.

More specifically, when polyethylene terephthalate (PET) is used as a raw material of the water-impermeable material 12, the water-impermeable material 12 can mechanically be formed in the form of uniform fibers having substantially the same thickness and length. The fiber diameter and fiber length of the fibrous water-impermeable material 12 are not particularly limited. For example, the fibrous water-impermeable material 12 is preferably formed to have a fiber diameter of about 10 to 500 μm and a fiber length of about 20 μm to 5 mm, and is more preferably formed to have a fiber diameter of about 50 to 100 μm and a fiber length of about 50 μm to 1 mm. The reason why the fiber diameter and the fiber length are set to values within the above ranges will be described later.

As described above, the channel part 10 of the functional material 1 according to this embodiment is formed so that a plurality of pieces of the water-impermeable material 12 are located between a plurality of pieces of the water-permeable material 11. As described above, the water-permeable material 11 constituting the channel part 10 can be formed as a bundle of the fibers f having a predetermined thickness. When the water-permeable material 11 is formed as a bundle of the fibers f having such a thickness, as shown in the enlarged view in FIG. 2(A) and FIG. 2(B), minute gaps (e.g., about several micrometers to several tens of micrometers) can be formed between the fibers f constituting the water-permeable material 11.

Figure 2B:
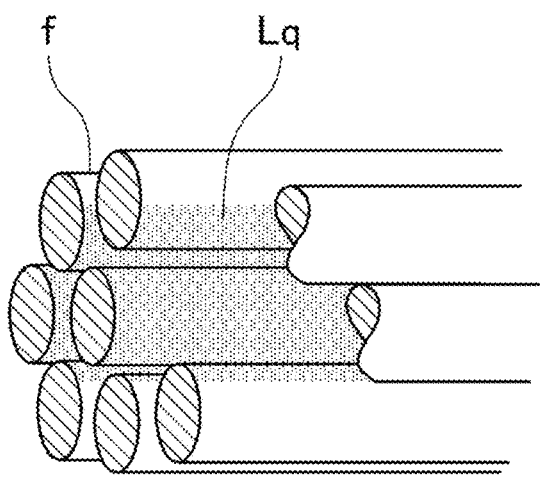
FIG. 2(B) is a schematic perspective view of a major part of the water-permeable material 11, which shows a situation in which a liquid Lq contained in the liquid sample penetrates into the water-permeable material 11.

When a liquid Lq such as water comes into contact with such a water-permeable material 11, as shown in FIG. 2(B), the liquid Lq enters the minute gaps between the fibers f so as to penetrate into the gaps. Then, the liquid Lq that has once entered the gaps between the fibers f is allowed to automatically move through the gaps due to the interaction, such as surface tension, between the surface of the fibers f forming the gaps and the liquid Lq.

Such a phenomenon corresponds to so-called capillarity. Therefore, the moving distance of the liquid Lq that has penetrated between the fibers f depends on the surface tension of the fibers f, the wettability of the surface of the fibers f, and the density of the liquid Lq, and particularly depends on the width of the gaps between the fibers f.

Further, as shown in FIG. 2, the channel part 10 is made of the water-permeable material 11 containing the water-impermeable material 12. That is, the water-impermeable material 12 is placed between pieces of the water-permeable material 11, and therefore a plurality of voids $10h$ can be formed between the water-permeable material 11 and the water-impermeable material 12. The voids $10h$ are influenced by the size or shape of the water-permeable material 11 or the water-impermeable material 12, but can be formed so that the width of the voids is as very small as about 10 μm to 2 mm.

In addition, when the length of the water-impermeable material 12 is shorter than that of the water-permeable material 11, the voids $10h$ can be formed so that the adjacent voids $10h$ communicate with each other. Therefore, a network of the voids $10h$ can be formed in the channel part 10.

For this reason, when the liquid Lq comes into contact with the voids $10h$ of the channel part 10, as in the case of the water-permeable material 11, the liquid Lq that is in contact with the voids $10h$ is allowed to enter the voids $10h$ by capillarity, and in addition, is allowed to automatically move within the voids $10h$.

Therefore, when supplied to the base end $10a$ (see FIG. 1) of the channel part 10 of the functional material 1, a liquid sample is allowed to penetrate into the water-permeable material 11 (e.g., into gaps between a plurality of fibers f forming the water-permeable material 11) and the voids $10h$ (i.e., the voids $10h$ between pieces of the water-permeable material 11 formed by the water-impermeable material 12). As a result, the liquid sample moves in a direction away from the base end $10a$ (i.e., a direction toward the tip ends $10b$ of the channel part 10) while penetrating into the channel part $10a$. That is, when the water-permeable material 11 includes fibers and the water-impermeable material 12 is located in the water-permeable material 11, the channel part 10 can have a water-absorbing function. Particularly, a high water-absorbing function that cannot be obtained only by the water-permeable material 11 can be imparted to the channel part 10.

Further, the voids in the channel part 10 form a network-like channel (hereinafter, referred to as a void channel). Furthermore, the water-impermeable material 12 is non-uniformly (randomly) present in the channel part 10, and therefore the void channel through which a liquid sample flows is formed so that the channel width thereof varies (non-uniformly varies) in the longitudinal direction of the channel.

Therefore, when a liquid sample is supplied to the channel part 10, components present in the liquid sample can be screened by their size due to a filtering effect while the liquid sample moves through a channel formed by the gaps (hereinafter, referred to as a gap channel) and the network-like void channel. That is, a filtering function is imparted to the channel part 10, and therefore components other than a desired component (undesired components) present in a liquid sample can be removed to be separated from the desired component.

As described above, the channel part 10 of the functional material 1 according to this embodiment is formed to have a planar, that is, two-dimensional shape and a water-absorbing function and a filtering function. This eliminates the need for forming a channel part having a complicated three-dimensional structure by a technique using photolithography to impart a filtering function to the channel part. Therefore, the channel length of the channel part 10 can be made smaller than that of the channel part having a three-dimensional structure, which makes it possible to reduce the amount of a liquid sample to be supplied.

Further, a liquid sample moves within the channel part 10 by capillarity. Therefore, a liquid sample can move within the channel part 10 even when the functional material 1 is placed upright. For example, the functional material 1 may be placed upright so that the base end 10a of the channel part 10 having a substantially Y shape in plan view as shown in FIG. 1 is located on the lower side. Also in this case, a liquid sample is allowed to move from the base end 10a to the tip ends 10b of the channel part 10.

That is, the direction in which the functional material 1 according to this embodiment is placed during use is not limited to a horizontal direction. This makes it possible to increase the degree of freedom in placing the functional material 1 after a liquid sample is supplied to the channel part 10. For example, after a liquid sample is supplied to the two or more channel parts 10, the functional material 1 may be placed upright on a laboratory table while the liquid sample is allowed to move in the channel parts 10, which makes it possible to secure a workspace on the laboratory table.

The gaps in the water-permeable material 11 and the voids 10h in the channel part 10 correspond to channels through which a liquid sample flows (hereinafter, referred to as a gap channel and a void channel, respectively).

(Mixing Ratio Between Water-Permeable Material 11 and Water-Impermeable Material 12)

As described above, the flow channel 10 includes the water-permeable material 11 and the water-impermeable material 12, and therefore the channel width of the void channel can appropriately be adjusted by adjusting the mixing ratio between the water-permeable material 11 and the water-impermeable material 12 or the size of the water-impermeable material 12.

Further, the void ratio of the channel part 10 can also be adjusted to a desired value by adjusting the mixing ratio between the water-permeable material 11 and the water-impermeable material 12 or the size of the water-impermeable material 12. Furthermore, water absorbability changes with a change in the void ratio.

OTHER EMBODIMENTS

As described above, the functional material 1 is formed so that, as shown in FIG. 1, the base end and the tip ends of the channel part 10 are located inside the edge of the base material 2. However, as shown in FIG. 5, the functional material 1 may be formed so that a base end 10e and tip ends 10e of the channel part 10 are substantially flush with the edge of the base material 2.

Figure 5A:
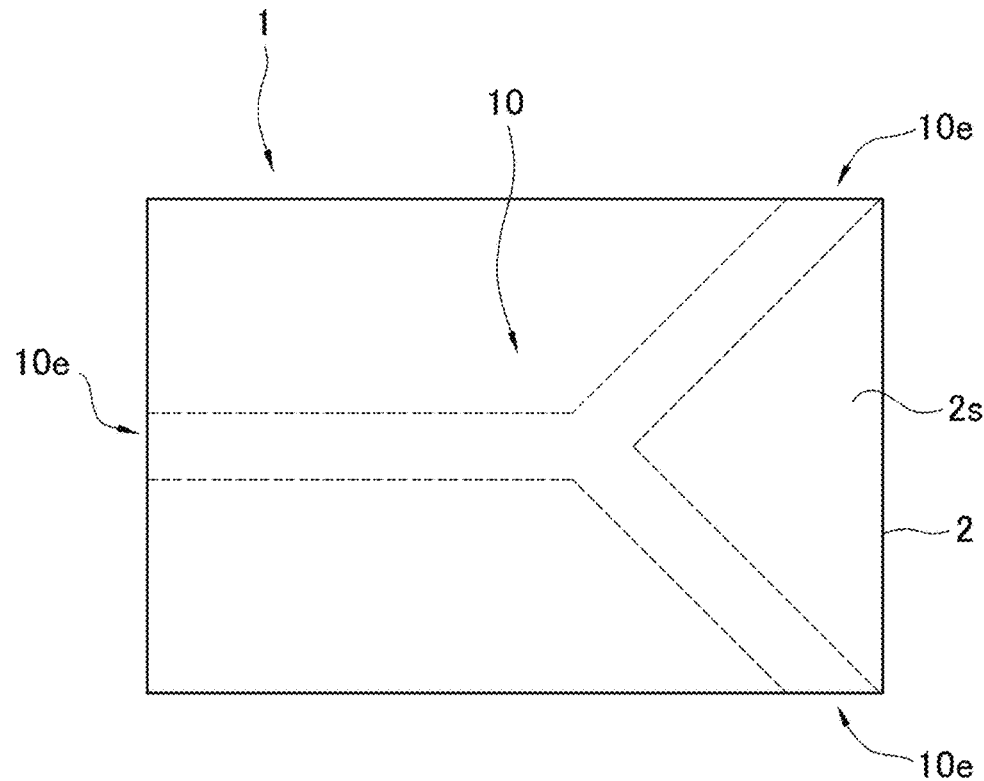
FIG. 5(A) is a schematic plan view illustrating a functional material 1 according to another embodiment of the present invention.
Figure 5B:
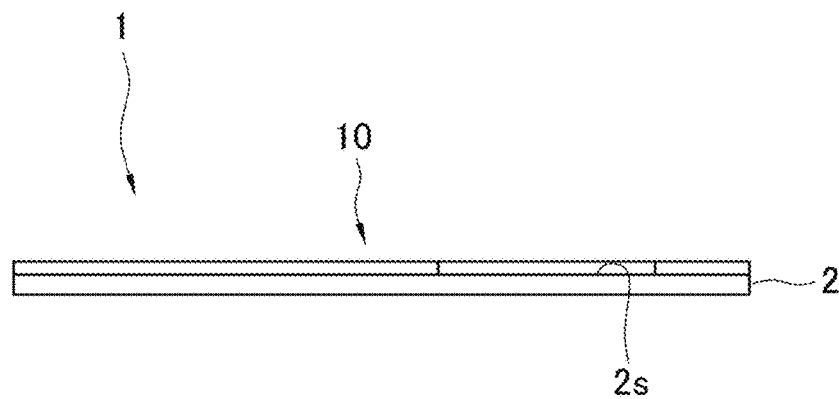
FIG. 5(B) is a schematic side view of the functional material 1 shown in FIG. 5(A).
Figure 7A:
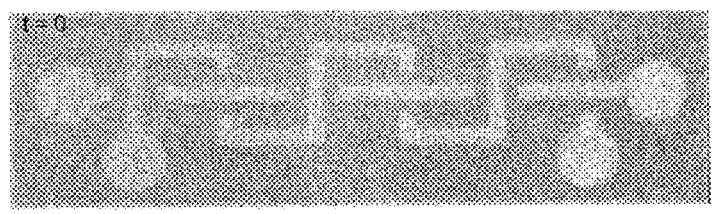
FIG. 7 shows schematic views illustrating a conventional technique in which a channel part is three-dimensionally formed using photolithography.
Figure 7B:
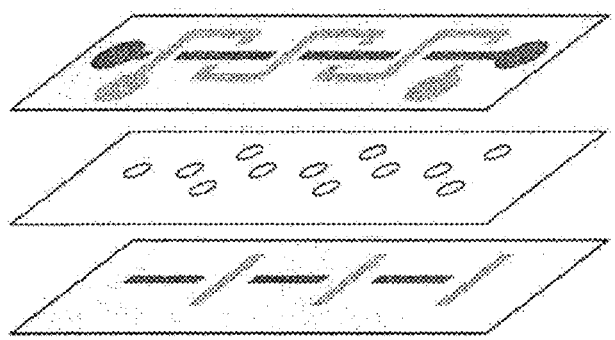
Figure 7C:
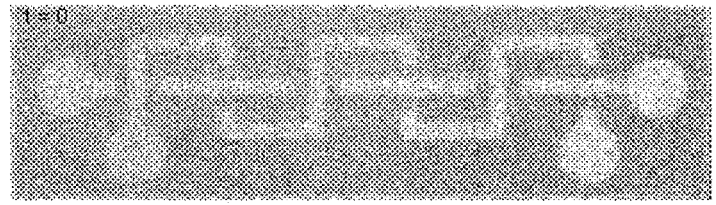
Figure 7C:
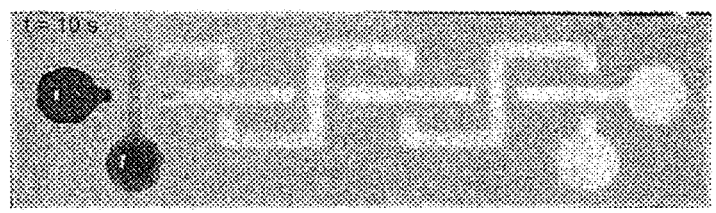
Figure 7C:
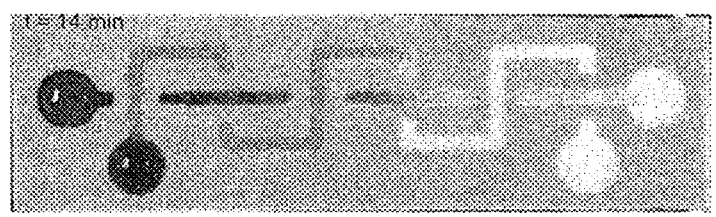

For example, as shown in FIG. 5, the channel part 10 having a substantially Y shape in plan view is provided on the surface 2s of the base material 2 having a rectangular shape in plan view so as to be parallel to the longitudinal direction of the base material 2. At this time, as shown in the side view of the functional material 1 in FIG. 5(B), the channel part 10 is provided on the surface 2s of the base material 2 so that the edge of the base end 10e of the Y-shaped channel part 10 is substantially flush with the short side of the base material 2. On the other hand, the channel part 10 is provided on the surface 2s of the base material 2 so that, like the edge of the base end 10e, the edges of the pair of tip ends 10e of the Y-shaped channel part 10 are substantially flush with the long sides of the base material 2, respectively.

Such a structure makes it possible to easily supply a liquid sample to the channel part 10 simply by immersing the functional material 1 in the liquid sample so that the short side of the base material 2 where the base end 10e of the channel part 10 is located comes into contact with the liquid sample. Further, it is possible to separate the supplied liquid sample at a branch point on the way so that the liquid sample can be discharged from each of the pair of tip ends 10e of the channel part 10.

On the other hand, when the functional material 1 is immersed in different liquid samples so that the long sides of the base material 2 where the pair of tip ends 10e of the channel part 10 are located come into contact with the different liquid samples, respectively, both the liquids can be discharged from the base end 10e of the channel part 10 in a mixed state.

Therefore, as described above, a desired component present in a liquid sample can be separated and purified simply by providing the functional material 1 in part of the route of analysis. Further, it is not necessary to allow the base end of the channel part 10 to hold a liquid sample or to allow each of the tip ends of the channel part 10 to carry a detection material, which is advantageous in that the structure of the functional material 1 can be made simple.

(Description of Functional Material 1 Using Nano-Fibers nf)

The above examples have been described with reference to a case where the channel part 10 of the functional material 1 according to this embodiment includes the water-permeable material 11 and the water-impermeable material 12 provided between pieces of the water-permeable material 11. However, the water-permeable material 11 is not limited to one described above as long as the channel part 10 allows a liquid to pass therethrough and, as described above, a desired component present in a liquid sample can be separated and purified. For example, nano-fiber layers including nano-fibers, which will be described later, may be used instead of the water-permeable material 11. Hereinbelow, the nano-fiber layers will specifically be described.

It is to be noted that the base material 2 and the water-impermeable material 12 constituting the channel part 10 have the same structures as described above, and therefore description thereof will not be repeated below.

Figure 3A:
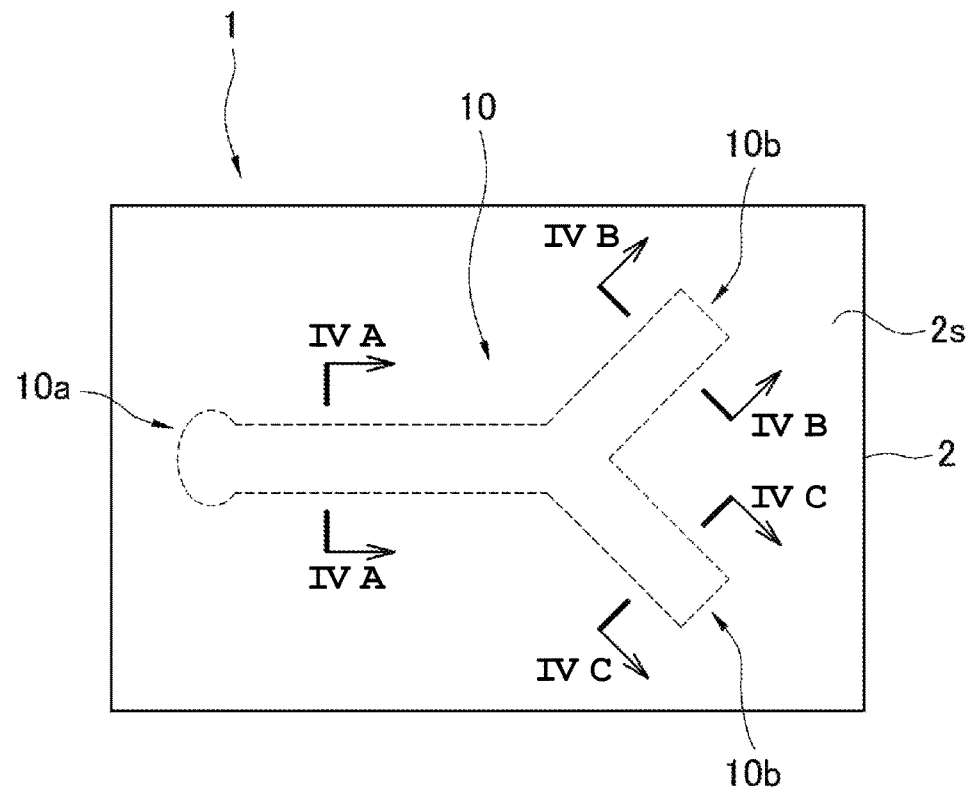
FIG. 3(A) is a schematic plan view illustrating the functional material 1 according to the embodiment of the present invention.
Figure 3B:
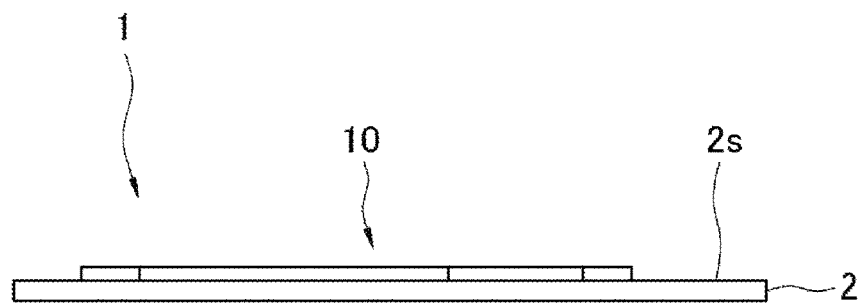
FIG. 3(B) is a schematic side view of the functional material 1 shown in FIG. 3(A).
Figure 4A:
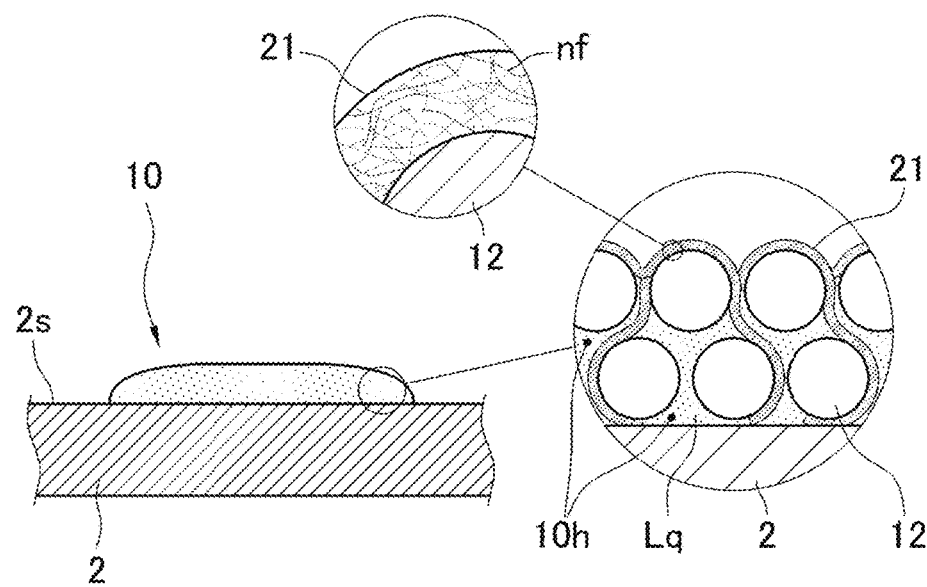
FIG. 4(A) is a schematic sectional view taken along a line IIB-IIB in the major-part enlarged view in FIG. 3(A) and FIG. 4(C) is a schematic sectional view taken along a line IIC-IIC in FIG. 1(A).
Figure 4B:
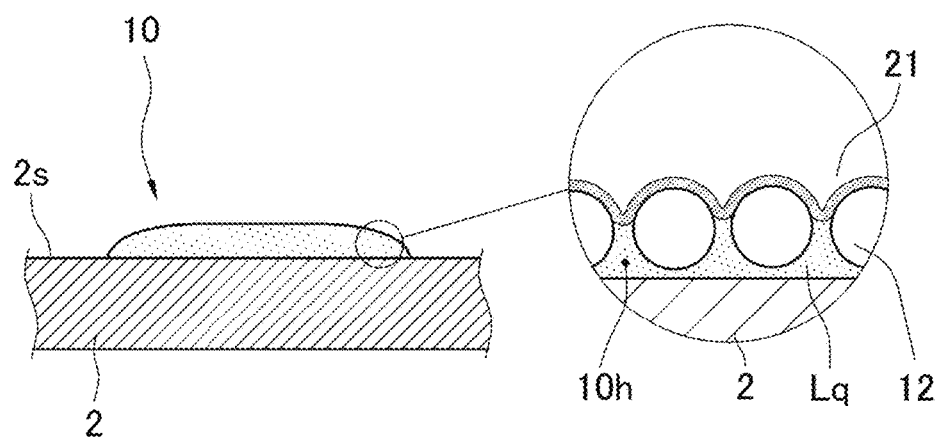
Figure 4C:
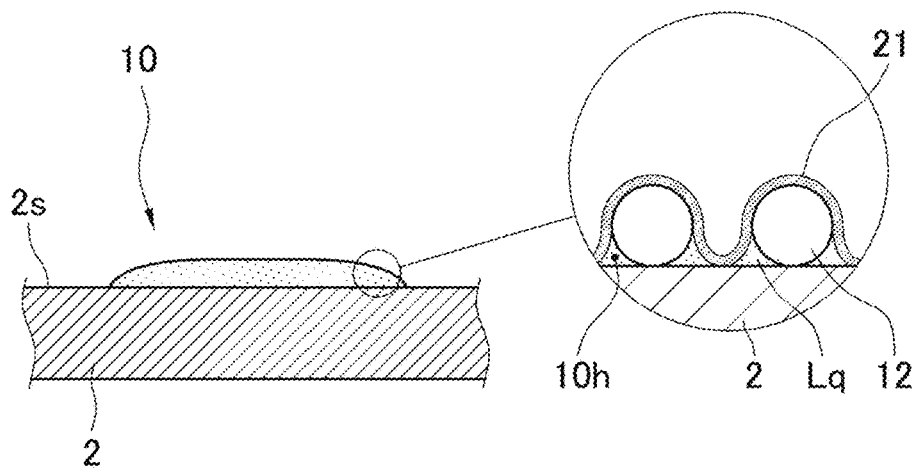

As shown in FIG. 3 and FIG. 4, the channel part 10 of the functional material 1 includes nano-fiber layers 21 including nano-fibers nf and the water-impermeable material 12 trapped between the nano-fiber layers 21.

As shown in FIG. 4(A), the nano-fiber layers 21 of the channel part 10 are assemblies of tangled nano-fibers nf, and are formed so that the surface of the channel part 10 and the water-impermeable material 12 are covered therewith. As will be described later, the nano-fibers nf forming the nano-fiber layers 21 are very fine fibers, and therefore assemblies formed by tangling such fibers have very low water permeability. Therefore, even when a liquid sample supplied to the channel part 10 of the functional material 1 is allowed to move within the channel part 10, it is possible to prevent the liquid sample from leaking from the inside to the outside of the channel part 10.

Further, as shown in FIG. 4, a plurality of pieces of the water-impermeable material 12 are bundled with the nano-fiber layers 21 in the channel part 10. Between the bundled pieces of the water-permeable material 12, gaps that function like the above-described voids 10h can be formed.

Therefore, these voids 10h can function as a channel through which a liquid sample supplied to the channel part 10 of the functional material 1 moves. Further, such a channel is very narrow, and therefore a liquid sample is allowed to move through the voids 10h in the channel part 10 while penetrating into the voids 10h by capillarity. Like the above-described void channel, such a channel has a network-like structure.

Therefore, as in the case where the channel part 10 uses the water-permeable material 11, components present in a liquid sample that moves through the channel can be screened by their size due to a filtering effect.

Therefore, even when the nano-fiber layers 21 including nano-fibers of are used as a material constituting the channel part 10 of the functional material 1, a water-absorbing function and a filtering function can be imparted to the channel part 10 as in the case where the water-permeable material 11 is used.

(Hydrophilic Functional Group)

It is to be noted that the nano-fiber layers 21 of the channel part 10 preferably have hydrophilic functional groups on their surface.

When such nano-fiber layers 21 are used, a film having hydrophilic functional groups is preferably formed on the surface 2s of the base material 2.

In this case, the nano-fiber layers 21 having the surface of the channel part 10 and the surface 2s of the base material 2 are covered with a plurality of hydrophilic functional groups. When coming into contact with each other, the functional groups of both the nano-fiber layers 21 and the surface 2s are strongly bonded together by hydrogen bonding.

Therefore, the channel part 10 and the base material 2 can reliably be coupled together simply by providing the channel part 10 on the surface 2s of the base material 2 by application or the like. This eliminates the need for an adhesive or the like using an organic solvent for coupling the channel part 10 to the surface 2s of the base material 2. In this case, it is possible to prevent contamination of the inside of the channel part 10 caused by penetration of a solvent of an adhesive into the channel part 10, which improves the accuracy of analysis of a liquid sample as compared to a case where an adhesive or the like is used.

It is to be noted that the nano-fiber layers 21 having hydrophilic functional groups on their surface preferably includes cellulose nano-fibers nf. The cellulose nano-fibers nf can easily be obtained by mechanically processing pulp or the like. The main component of pulp or the like as a raw material is cellulose having many hydroxyl groups. Therefore, the cellulose nano-fibers nf can more easily be obtained and are more economical as compared to a case where hydrophilic hydroxyl groups are chemically bonded to the surface of synthetic resin nano-fibers nf.

Further, the cellulose nano-fibers nf having a plurality of hydroxyl groups on their surface is more hydrophilic than general synthetic resin nano-fibers nf having hydrophilic functional groups chemically bonded thereto. That is, the cellulose nano-fibers nf have the property of easily getting wet with water. Therefore, when the nano-fiber layers 21 of the channel part 10 are formed using the cellulose nano-fibers nf, it is possible to further improve capillary action that occurs when a liquid sample flows through the voids 10h (i.e., the void channel) formed between the nano-fiber layers 21.

Examples of the hydrophilic functional groups include commonly-used hydrophilic functional groups such as a hydroxyl group and a carboxyl group.

It goes without saying that the above-described water-permeable material 11 may have such hydrophilic functional groups on its surface. For example, the water-permeable material 11 to be used may be one having hydrophilic functional groups on its surface. When such a water-permeable material 11 is used, a film having hydrophilic functional groups is formed on the surface 2s of the base material 2. This produces the same effect as in the case described above.

Further, the cellulose nano-fibers nf to be used can be obtained by various methods, and may be those obtained by mechanically processing pulp or the like, those obtained by chemically processing pulp or the like, those obtained by mechanically processing a dissolved synthetic resin such as polyethylene, or biological bacterial cellulose.

For example, cellulose nano-fibers nf obtained by mechanically processing pulp have an average fiber diameter of about 1 to 100 nm and an average fiber length of about 100 nm to 1 μm.

(Method for Producing Functional Material 1)

As described above, the functional material 1 according to this embodiment is formed by providing the channel part 10 on the surface 2s of the base material 2. Further, as described above, various materials in various sizes may be used as the water-permeable material 11 or the nano-fiber layers 21 and the water-impermeable material 12 constituting the channel part 10.

Hereinbelow, a method for producing the functional material 1 will be described with reference to a typical case where the channel part 10 including the nano-fiber layers 21 including nano-fibers nf and the water-impermeable material 12 trapped between the nano-fiber layers 21 is provided on the surface 2s of the base material 2.

It goes without saying that a method for producing the functional material 1 according to this embodiment is not limited to the following production method.

First, the nano-fibers nf forming the nano-fiber layers 21 will be described.

The nano-fibers nf used to form the nano-fiber layers 21 may be those obtained by mechanically processing fibers mainly made of cellulose as a raw material into fine fibers (hereinafter, referred to as cellulose nano-fibers nf). A method for processing the fibers as a raw material into fine fibers is not particularly limited, but pulp fibers can be processed into nano-fibers nf by using, for example, a low-pressure homogenizer, a high-pressure homogenizer, a grinder, a cutter mill, a jet-mill, a short-screw extruder, a twin screw extruder, or an ultrasonic stirrer.

The fibers as a raw material of nano-fibers nf are not particularly limited as long as the fibers are mainly made of cellulose, and examples thereof include pulp fibers, wood powder, plant residues, and papermaking residues.

Next, the water-impermeable material 12 of the channel part 10 will be described.

As the water-impermeable material 12, PET fibers having a larger diameter than the nano-fibers nf forming the nano-fiber layers 21 (hereinafter, simply referred to as PET fibers) may be used.

As described above, the PET fibers to be used are preferably those formed to have a fiber diameter of about 10 to 500 μm and a fiber length of about 20 μm to 5 mm, and are more preferably those formed to have a fiber diameter of about 50 to 100 μm and a fiber length of about 50 μm to 1 mm.

The base material 2 to be used can be selected from the above-described various materials. When a water-permeable material is used as the base material 2, the surface 2s may be covered with a water-impermeable film. For example, when the paper-made base material 2 is used, the above-described cellulose nano-fibers nf may be applied thereonto. The application of the cellulose nano-fibers nf onto the surface of the paper-made base material 2 makes it possible to form a cellulose nano-fiber layer on the surface 2s of the base material 2. That is, water resistance required for the base material 2 can easily be imparted simply by applying the cellulose nano-fibers onto the paper-made base material 2. Even when the functional material 1 is used in which the channel part 10 is provided on such a coated surface, it is possible to prevent a liquid sample supplied to the channel part 10 from leaking from the inside of the channel part 10 and penetrating into the paper-made base material 2.

Further, the cellulose nano-fibers nf have a plurality of hydroxyl groups as hydrophilic functional groups on their surface. Therefore, when the channel part 10 having the cellulose nano-fiber nf layers 21 is provided on the surface 2s of the base material 2, the channel part 10 and the base material 2 can tightly be coupled together by hydrogen bonding.

Then, the cellulose nano-fibers nf obtained by the above method and the PET fibers are dispersed in water to form a dispersion liquid.

The concentration of the cellulose nano-fibers nf in the dispersion liquid may be adjusted to obtain formability suitable for forming the channel part 10 of the functional material 1. However, if the concentration of the cellulose nano-fibers nf is less than 0.1 wt %, it is difficult to maintain the shape of the channel part 10 when the dispersion liquid is applied onto the paper-made base material 2. On the other hand, if the concentration of the cellulose nano-fibers nf is larger than 5 wt %, the cellulose nano-fibers nf are tangled with openings provided in the transfer section of a screen printer, which will be described later, due to high viscosity so that the channel part 10 cannot be formed using the screen printer, or the cellulose nano-fibers nf hold too much moisture so that it is difficult to dry the channel part 10 or maintain the shape of the channel part 10 after drying. For this reason, the concentration of the cellulose nano-fibers nf in the dispersion liquid is adjusted to 0.1 or more but 5 wt % or less, preferably 0.5 to 3 wt %, more preferably 1 to 2 wt %.

Further, the mixing ratio between the cellulose nano-fibers nf and the water-impermeable material 12 can be appropriately adjusted depending on the water absorbability of the channel part 10 or the size of a desired component contained in a liquid sample. For example, as shown in FIG. 4, the ratio of the voids 10h formed between the cellulose nano-fiber layers 21 can be adjusted by gradually reducing the mixing ratio of the water-impermeable material 12 (in FIG. 4, the mixing ratio is reduced in the order of (A), (B), and (C)).

The obtained dispersion liquid is supplied onto the top surface of the base material 2 horizontally placed. Various methods can be used to supply the dispersion liquid to form the channel part 10 on the surface 2s of the base material 2, such as a method in which the dispersion liquid is applied by a screen printing technique, a method in which the dispersion liquid is applied using a spray, a method using an intaglio printing technique, and a method using a flexographic printing technique.

Hereinbelow, a method in which the dispersion liquid is applied using a screen printing technique will be described which is the simplest method out of the above methods.

As a screen printer, a commonly-used one can be used. More specifically, the screen printer includes a transfer section and a frame provided to surround the transfer section. The transfer section has holes (openings) provided in a meshed pattern to allow the front and back surfaces thereof to communicate with each other, and the openings are covered with a photosensitive resin. The transfer section has a portion that has the shape of the channel part 10 and that is free from the photosensitive resin. That is, the portion free from the photosensitive resin has a plurality of openings provided to allow the front and back surfaces of the transfer section to communicate with each other. The openings may have a common size, for example, an opening diameter of 1.29 mm.

The paper-made base material 2 is disposed under the transfer section of the screen printer, and the dispersion liquid is supplied to the transfer section of the screen printer. Then, a squeegee provided in the screen printer is moved so as to slide on the top surface of the transfer section. As a result, the dispersion liquid is applied in a desired shape onto the surface 2s of the base material 2 through the openings.

The base material 2 having the dispersion liquid adhered thereto is dried to produce the functional material 1. The functional material 1 can be formed so that an inner layer of the base material 2, a water resistant layer having the surface 2s of the base material 2, and the channel part 10 are provided in this order in the sectional view of the functional material 1 that is horizontally placed so that the back surface (the surface on which the channel part 10 is not provided) of the base material 2 is located on the lower side. As shown in, for example, FIG. 4, the channel part 10 is formed to have an internal section in which a plurality of pieces of the water-impermeable material 12 are covered with the cellulose nano-fiber layers 21. Therefore, the voids 10h are formed between the cellulose nano-fiber layers 21, in other words, between the pieces of the water-impermeable material 12 placed so as to be held by the cellulose nano-fiber layers 21. The voids 10h function as avoid channel through which a liquid sample supplied to the channel part 10 moves.

It is to be noted that the cellulose nano-fibers nf of the channel part 10 shrink due to moisture loss during drying, and are coupled to the cellulose nano-fibers nf on the surface 2s of the base material 2 by hydrogen bonding in a portion of the channel part 10 that is in contact with the surface 2s of the base material 2. The hydrogen bonding between the cellulose nano-fibers nf of the channel part 10 and the cellulose nano-fibers nf on the surface 2s of the base material 2 makes it possible to tightly couple the channel part 10 to the paper-made base material 2.

A drying method to be used is not particularly limited, and may be, for example, a known drying method involving heating. Examples of such a method include drying with hot air (air drying), drying using a heating roller, and hot pressing.

A drying time is not particularly limited, either, and may be appropriately determined depending on the condition of the channel part 10 or the required performance of the functional material 1. For example, in order to exert water absorbability and filtering properties, drying may be performed so that the moisture content of paper after drying is about 0 to 10%.

(Method for Producing Functional Material 1 Including Only Channel Part 10)

The above example has been described with reference to a case where the base material 2 whose surface 2s is water resistant and hydrophilic is used. However, the base material 2 whose surface 2s is water resistant and hydrophobic may be used.

In this case, when the channel part 10 is provided on the surface 2s of the base material 2 and then dried by the above method, hydrophilic functional groups on the surface of the channel part 10 are not coupled with hydrophobic functional groups on the surface 2s of the base material 2. Therefore, when an adhesive or the like is not used, the functional material 1 including only the channel part 10 can be produced simply by peeling off the channel part 10 formed to have a desired shape from the surface 2s of the base material 2.

(Functional Liquid)

In the above example, the water that disperses the cellulose nano-fibers nf and the PET fibers corresponds to a liquid that disperses a water-impermeable material and nano-fibers in claims.

Further, the dispersion liquid, that is, the dispersion liquid obtained by dispersing the cellulose nano-fibers nf and the PET fibers in water corresponds to a mixed fluid and a functional fluid in claims.

In the above example, the functional fluid is formed by dispersing the cellulose nano-fibers nf and the PET fibers in water. However, the functional fluid may be formed by dispersing the water-permeable material 11 including the above-described material (e.g., natural fibers or chemical fibers) and the water-impermeable material 12 including the above-described material (e.g., polyethylene terephthalate (PET)) in a liquid such as water. By printing such a functional fluid used like ink on the base material 2 by a method such as screen printing, the channel part 10 including the water-permeable material 11 and the water-impermeable material 12 can be formed on the base material 2. In addition, printing makes it possible to freely form a channel on the base material 2.

It is to be noted that an object on which the functional fluid is to be printed is not limited to the base material 2, and the functional fluid can be printed on various objects.

Particularly, when the channel part 10 is formed using a dispersion liquid obtained by dispersing the water-permeable material 11 including a fibrous material and the water-impermeable material 12 including a fibrous material in water or the like, voids having a small diameter can be formed in the channel part 10. That is, voids into which a liquid can penetrate by capillarity can be formed between the fibers. This allows the channel part 10 to have a high water-absorbing function.

EXAMPLES

Experiments were performed to determine the water-absorbing function and filtering function of the functional material according to the present invention.

In the experiments, a solution prepared by dispersing cellulose nano-fibers and a water-impermeable material (PET fibers) (concentration of cellulose nano-fibers: about 1.28 wt %) was applied onto the surface of a base material having a water-resistant surface by screen printing and then dried to form a channel part to produce a functional material.

It is to be noted that the base material having a water-resistant surface was prepared in the following manner. A solution was prepared by dispersing, in water, cellulose nano-fibers prepared using a device that will be described later, and the solution was applied onto the surface of a piece of paper having a length of 5 cm and a width of 5 cm and then dried. Such a solution was prepared so that the concentration of cellulose nano-fibers dispersed in water was about 2 wt %.

(Method for Producing Cellulose Nano-Fibers)

The cellulose nano-fibers were produced by grinding pulp using an ultra-fine friction grinder (manufactured by MASUKO SANGYO CO., LTD., trade name: Supermasscolloider, model: MKZA10-15J).

The grinding included preliminary grinding and final grinding.

First, preliminary grinding was performed three times using a rough grindstone (model: MKE10-46). The preliminary grinding was performed in a contact state, and a current value during processing was about 18 A. After the preliminary grinding, final grinding was performed 14 times using a fine grindstone (MKGC10-80). The final grinding was performed in a contact state, and a current value during processing was about 24 A.

The thus produced cellulose nano-fibers had a fiber diameter of about 10 to 500 nm and a fiber length of about 500 µm or less.

It is to be noted that the cellulose nano-fibers applied onto the surface of the base material were obtained by performing final grinding 30 times using the above-described device. The thus obtained cellulose nano-fibers had a fiber diameter of 100 nm or less.

(Water-Impermeable Material)

As the water-impermeable material, two kinds of PET fibers (manufactured by TEIJIN LIMITED) were used. The PET fibers used as first PET fibers had a fiber diameter of 50 µm and a fiber length of 50 µm (hereinafter, referred to as PET fibers (50 µm)). The PET fibers used as second PET fibers had a fiber diameter of 50 µm and a fiber length of 100 µm (hereinafter, referred to as PET fibers (100 µm)).

Each of the two kinds of PET fibers and the cellulose nano-fibers were mixed in each of the following mixing ratios (mass ratios) and then placed in a beaker containing a solvent (water). The mixture in the beaker was well stirred to prepare a dispersion liquid in which the cellulose nano-fibers and the PET fibers were sufficiently dispersed in the solvent.

Cellulose nano-fibers: PET fibers=5:5, 4:6, 3:7, 2:8, and 1:9

The prepared dispersion liquid was applied using a screen printing plate (manufactured by Tokai Shoji K.K., opening: 1293 µm, wire diameter: 400 µm) to form, on the surface of the base material, a channel part having an I shape in plan view. Then, the channel part formed on the surface of the base material was dried by allowing it to stand at room temperature to form a functional material.

It is to be noted that the moisture content of the functional material after drying was about 10%.

(Water Absorption Test)

The water-absorbing function of each of the functional materials formed by the above method was evaluated based on penetration height given by immersing the functional material in a dye solution obtained by dissolving a dye in water.

Each of the functional materials was allowed to stand for 10 minutes in a state where one of the tip ends of the channel part was immersed about 3 mm in the dye solution.

(Results)

The results of the experiment are shown in FIG. 8.

Figure 8A:
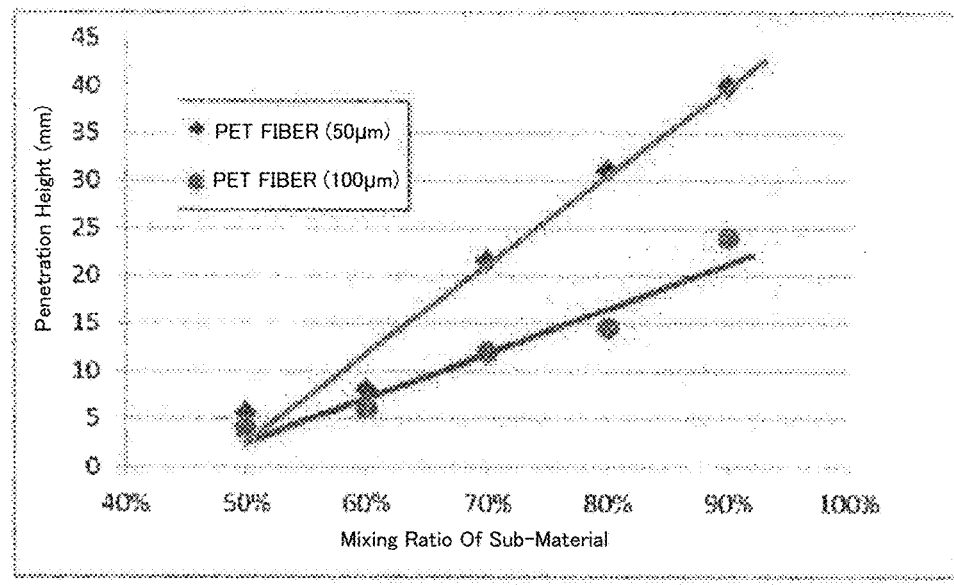
FIG. 8 shows graphs of experimental results.

As shown in FIG. 8(A), it was confirmed that water absorbability improved as the mixing ratio of the PET fibers increased.

Figure 8B:
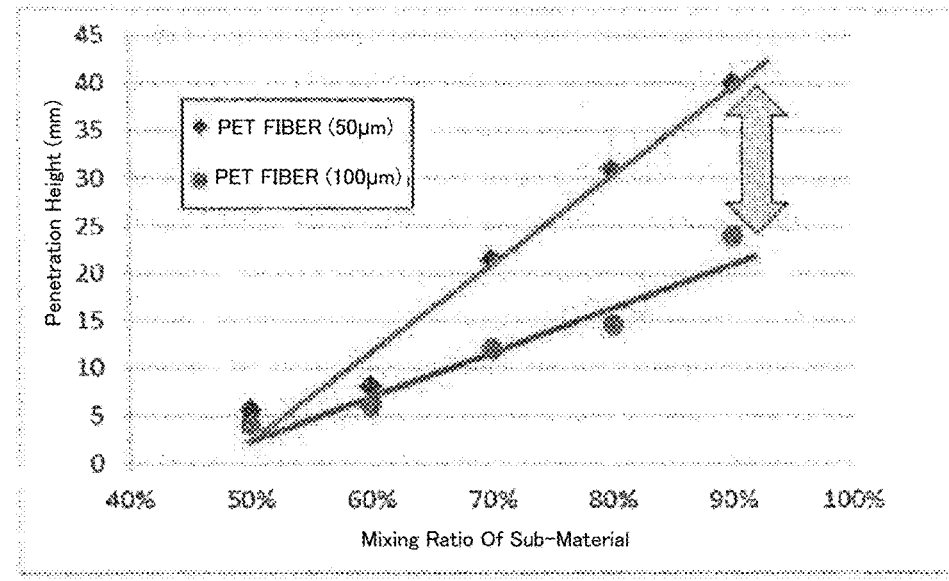

Further, as shown in FIG. 8(B), it was confirmed that the difference in fiber length caused the difference in water absorbability.

From the above results, it was supposed that in the channel part of the functional material, the PET fibers were held so as to be covered with cellulose nano-fiber layers including the cellulose nano-fibers, and a network of minute voids was formed between the cellulose nano-fiber layers, in other words, between the PET fibers held so as to be covered with the cellulose nano-fiber layers.

Further, it was confirmed that such a network of minute voids could be adjusted by varying the mixing ratio between the cellulose nano-fibers and the PET fibers. Therefore, it was confirmed that the filtering function of the channel part could be controlled by adjusting the network of voids of the channel part (see FIGS. 3 and 4).

(Filtering Function)

An experiment was performed to determine whether the functional material formed by the above method had a filtering function. In the experiment, a liquid containing a solid was dropped onto the functional material to determine how the solid moved.

The functional material was formed by the above method using a dispersion liquid (i.e., a method in which a dispersion liquid is applied onto a base material by screen printing). It is to be noted that the ratio between the water-permeable material and the water-impermeable material was 80%:20%.

The liquid dropped onto the functional material was prepared by mixing a pigment (black) having an average particle size of 4 μm with water at 1%.

(Results)

Figure 9A:
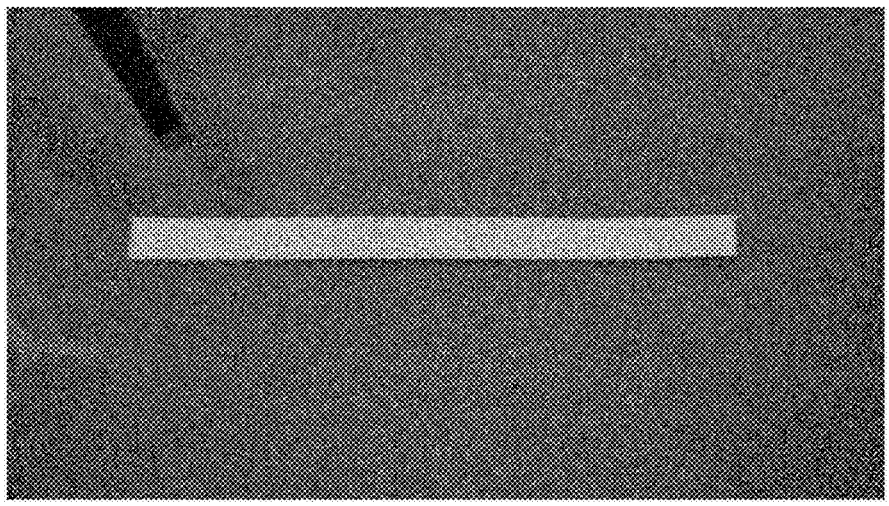
FIG. 9 shows photographs showing the results of an experiment for examining a filtering effect.
Figure 9B:
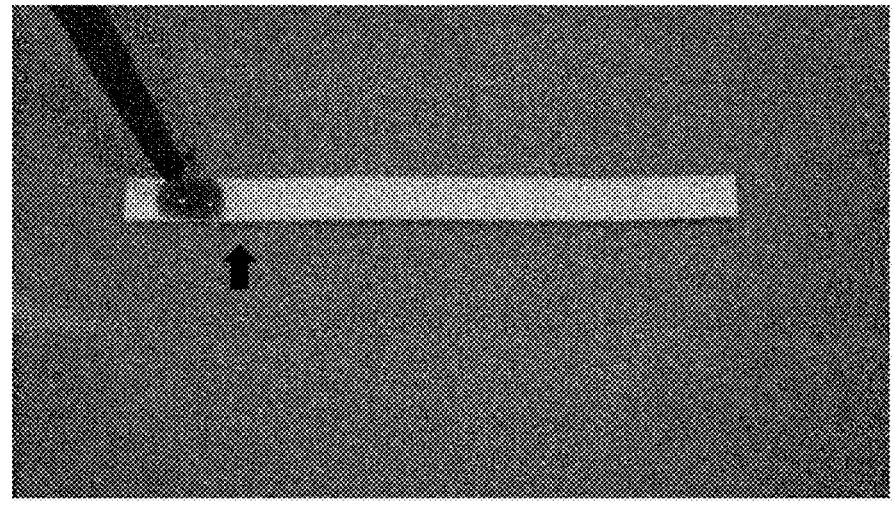
Figure 10A:
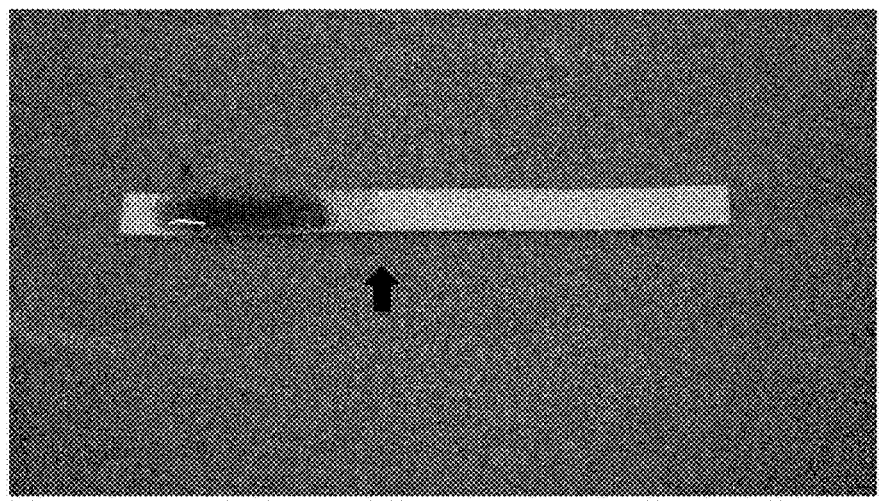
FIG. 10 shows photographs showing the results of the experiment for examining a filtering effect.
Figure 10B:
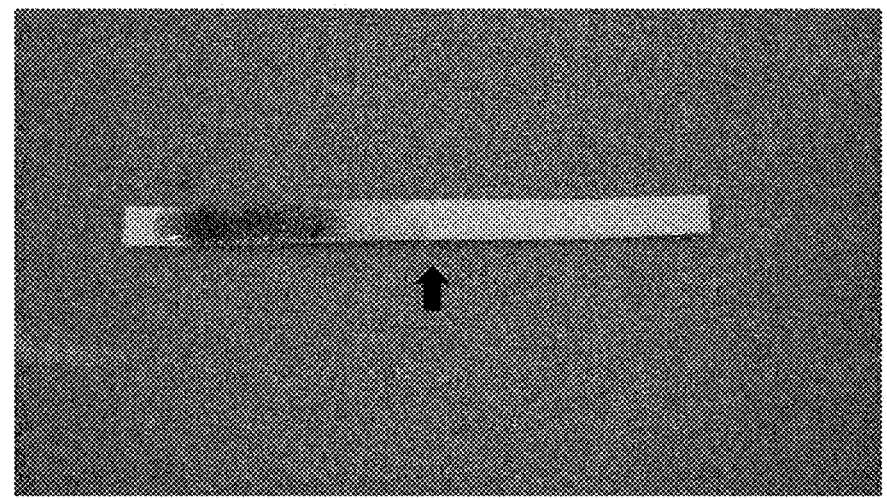

The results of the experiment are shown in FIGS. 9 to 12. As shown in FIGS. 9 to 12, it was conformed that just after the liquid was dropped, its penetration rate was high (i.e., its penetration distance was large) but a separation effect was low so that a black region expanded (FIGS. 9 and 10).

Figure 11A:
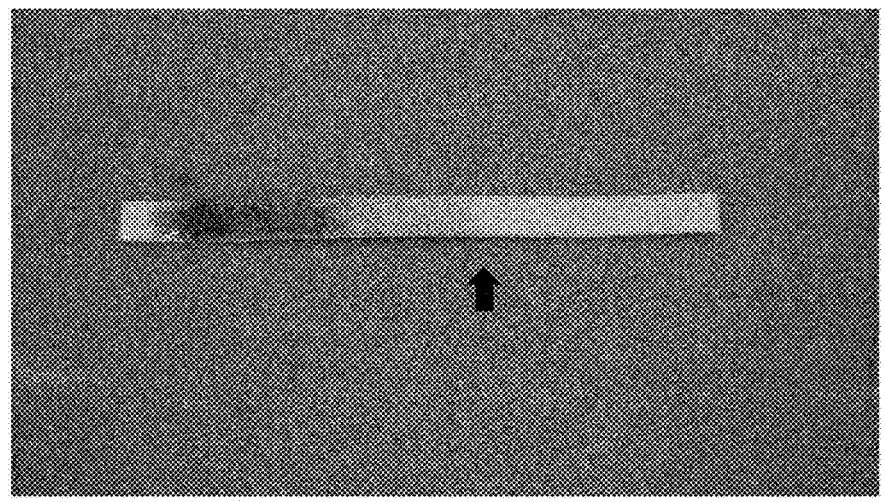
FIG. 11 shows photographs showing the results of the experiment for examining a filtering effect.
Figure 11B:
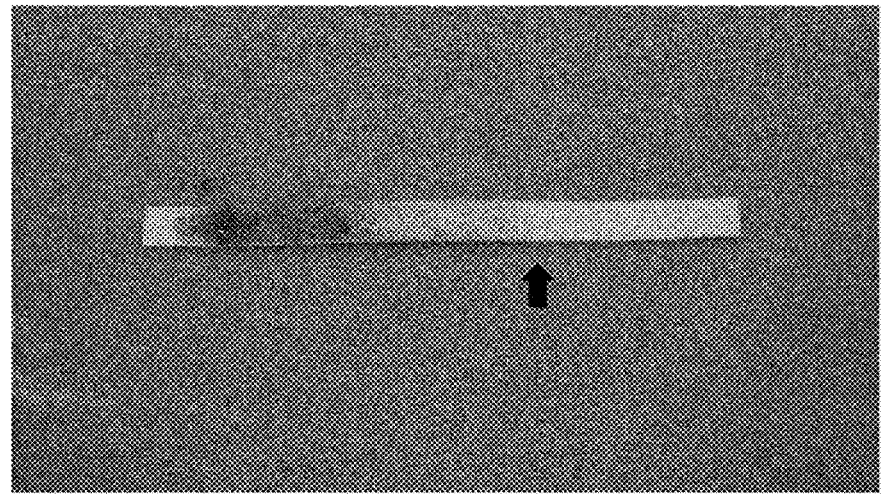
Figure 12A:
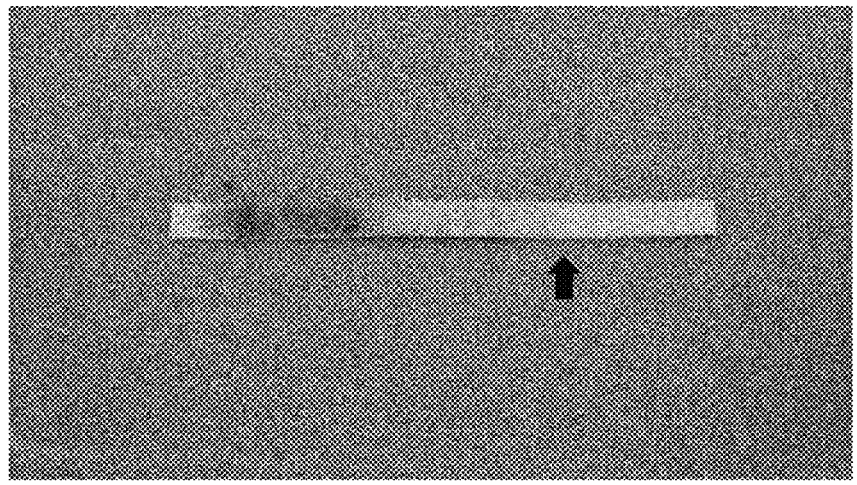
FIG. 12 shows photographs showing the results of the experiment for examining a filtering effect.
Figure 12B:
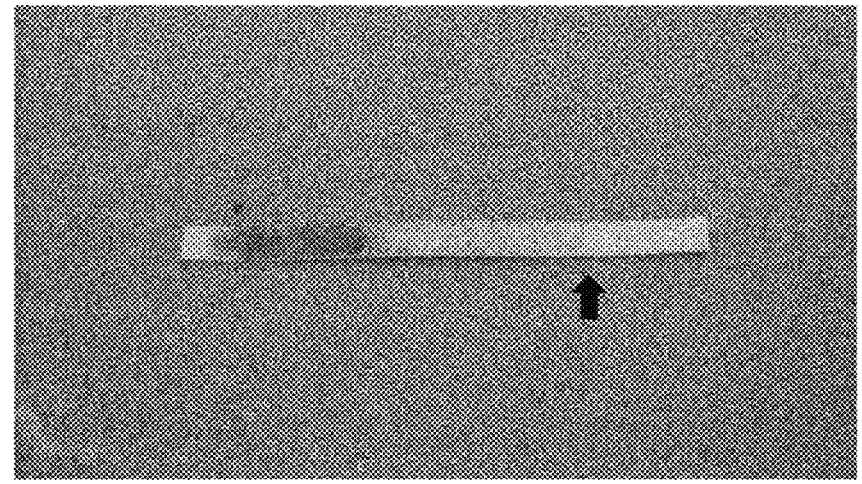

It was confirmed that the penetration distance increased with time so that the liquid penetrated to a position away from the position onto which the liquid was dropped (FIGS. 11 and 12). However, the colored portion remained in the vicinity of the position onto which the liquid was dropped, but a portion to which the liquid penetrated was not colored at the position away from the position onto which the liquid was dropped. That is, it was confirmed that the liquid penetrated, but the movement of the pigment contained in the liquid was prevented. From the results, it was confirmed that the channel part of the functional material according to the present invention allowed a liquid to pass therethrough, but had the function of preventing the movement of a solid contained in the liquid, that is, a filtering function.

INDUSTRIAL APPLICABILITY

The functional material according to the present invention is suitable as a material used for sample analysis in medical, biochemical, pharmaceutical, chemical, and environmental fields.

DESCRIPTION OF REFERENCE SIGNS

1 Functional material
2 Base material
2s Surface of base material
10 Channel part
10h Voids in channel part
11 Water-permeable material
12 Water-impermeable material
21 Nano-fiber layer
nf Nano-fiber

The invention claimed is:
1. A functional material comprising:
a base material that is in a sheet shape, having a mounting surface and a bottom surface; and
a channel part that is provided on the mounting surface of the base material and that allows a liquid sample to pass therethrough, wherein
the mounting surface of the base material is water-impermeable,
the channel part comprises
a nano-fiber layer (21) that is composed with nano-fibers, which are tangled in random directions such that the nano-fiber layer is water-impermeable, and
a plurality of longitudinal fibers (12) that are made of a water-impermeable material, the longitudinal fibers being in a longitudinal shape, of which fiber diameters vary within a range about from 10 μm to 500 μm and of which fiber lengths vary within a range about from 20 μm to 5 mm,
the channel part has a predetermined length in a longitudinal direction, which is determined with two ends that are a base end (10a) and a tip end (10b),
the longitudinal fibers are trapped between the nano-fiber layer and the mounting surface, and arranged in the longitudinal direction of the channel part, and
voids (10h), which are empty spaces, are formed around the longitudinal fibers by following the longitudinal shape of the longitudinal fibers, being in a mesh structure in which one of the voids connects to another of the voids such that the empty spaces are connected from the base end to the tip end.
2. The functional material according to claim 1, wherein an average width of the voids is ranged around from 10 μm to 2 mm such that the liquid sample is carried through the channel part due to capillarity.
3. The functional material according to claim 2, wherein the voids are all located between the nano-fiber layer and the mounting surface of the base material,
some of the voids intervene between the longitudinal fibers.
4. The functional material according to claim 3, wherein the longitudinal fibers are composed of one or more of materials, which are selected from a group consisting of polyethylene terephthalate, polyethylene, polypropylene, calcium carbonate and silicon dioxide.
5. The functional material according to claim 2, wherein the nano-fibers composing the nano-fiber layer are cellulose nano-fibers (nf) of which an average fiber diameter is ranged about from 1 to 100 nm, and of which an average fiber length is ranged about from 100 nm to 1 μm.
6. The functional material according to claim 2, wherein the nano-fiber layer has a surface on which hydrophilic function group are present,
hydrophilic function group are present on the mounting surface of the base material, and
the nano-fiber layer contacts to the mounting surface of the base material such that the hydrophilic function group of the nano-fiber layer and the hydrophilic function group of the mounting surface are bonded by hydrogen bonding therebetween.
7. The functional material according to claim 2, wherein a ratio, which is proportion by weight, between the nano-fibers and the longitudinal fibers is ranged from 1:9 to 5:5.
8. The functional material according to claim 2, wherein the channel part has a channel width that is determined parallel to the mounting surface and perpendicular to the longitudinal direction,
the channel width at the base end is larger than the channel width at a remaining of the channel part such that the base end holds larger amount of the liquid sample that the remaining of the channel part does.

9. The functional material according to claim 8, wherein a detection material, which reacts with a desired component, is contained at the tip end of the channel part such that the detection material reacts in a case where the liquid sample including the desired component reaches the tip end.

10. The functional material according to claim 3, wherein the channel part has
   a channel width that is determined parallel to the mounting surface and perpendicular to the longitudinal direction, and
   a channel thickness that is determined perpendicular to the mounting surface, the channel width of the channel part is ranged about from 0.5 mm to 50 mm, and the channel thickness of the channel part is ranged about from 20 μm to 5 mm.

11. The functional material according to claim 10, wherein
   the channel part branches toward the tip end to form two or more of tip ends, which are positioned at an opposite from the base end.

12. The functional material according to claim 11, wherein
   one of the tip ends, which is defined as a first tip end, contains a first detection material, which reacts with a first desired component, such that the first detection material reacts in a case where the liquid sample including the first desired component reaches the first tip end, and
   another of the tip ends, which is defined as a second tip end, contains a second detection material, which reacts with a second desired component, such that the second detection material reacts in a case where the liquid sample including the second desired component reaches the second tip end, and
   the first detection material is different in composition from the second detection material.

13. The functional material according to claim 3, wherein
   the nano-fibers further comprises another nano-fiber layer wherein the nano-fiber layer, which is defined as a first nano-fiber layer, covers an upper surface of the longitudinal fibers and the another nano-fiber layer, which is defined as a second nano-fiber layer, is located inside the longitudinal fibers,
   the nano-fibers composing the first and second nano-fiber layers have
      an average fiber diameter that is ranged about from 1 to 100 nm, and
      an average fiber length that is ranged about from 100 nm to 1 μm,
   the nano-fibers form the first and second nano-fiber layers, and
   in a cross sectional view in the longitudinal direction,
      one of the longitudinal fibers is parallel to another of the longitudinal fibers, and
      the second nano-fiber layer intervene between two of the longitudinal fibers, which are adjacent each other.

* * * * *